United States Patent
Kienzle, III et al.

(10) Patent No.: US 8,052,695 B2
(45) Date of Patent: Nov. 8, 2011

(54) ADJUSTABLE INSTRUMENTS FOR USE WITH AN ELECTROMAGNETIC LOCALIZER

(75) Inventors: Thomas C. Kienzle, III, Lake Forest, IL (US); Jon T. Lea, Hampstead, NH (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 2224 days.

(21) Appl. No.: 10/677,420

(22) Filed: Oct. 2, 2003

(65) Prior Publication Data

US 2004/0073228 A1    Apr. 15, 2004

Related U.S. Application Data

(60) Provisional application No. 60/417,960, filed on Oct. 11, 2002.

(51) Int. Cl.
*A61B 19/00* (2006.01)
(52) U.S. Cl. .......................................... 606/130; 606/96
(58) Field of Classification Search ................ 606/54, 606/130, 96; 600/420, 426
See application file for complete search history.

(56) References Cited

U.S. PATENT DOCUMENTS

| | | | |
|---|---|---|---|
| 2,238,870 A * | 4/1941 | Haynes ............................ | 606/59 |
| 4,710,075 A * | 12/1987 | Davison ........................ | 408/202 |
| 5,638,819 A | 6/1997 | Manwaring et al. | |
| 5,829,444 A | 11/1998 | Ferre et al. | |
| 5,895,389 A * | 4/1999 | Schenk et al. .................. | 606/96 |
| 6,175,756 B1 * | 1/2001 | Ferre et al. ..................... | 600/424 |
| 6,190,395 B1 * | 2/2001 | Williams ....................... | 606/130 |
| 6,235,038 B1 | 5/2001 | Hunter et al. | |
| 6,285,902 B1 | 9/2001 | Kienzle, III et al. | |
| 6,478,802 B2 | 11/2002 | Kienzle, III et al. | |
| 6,697,664 B2 | 2/2004 | Kienzle, III et al. | |
| 6,887,247 B1 * | 5/2005 | Couture et al. ................. | 606/96 |
| 2002/0055679 A1 * | 5/2002 | Sati et al. ....................... | 600/424 |
| 2003/0078565 A1 * | 4/2003 | Vilsmeier et al. ................ | 606/1 |
| 2004/0077940 A1 | 4/2004 | Kienzle, III et al. | |
| 2006/0122495 A1 | 6/2006 | Kienzle, III | |

FOREIGN PATENT DOCUMENTS

WO    WO 2004/046754 A2    6/2004

* cited by examiner

*Primary Examiner* — Thomas C. Barrett
*Assistant Examiner* — Christian Sevilla
(74) *Attorney, Agent, or Firm* — McAndrews, Held & Malloy, Ltd.; William Baxter

(57) ABSTRACT

A system for tracking the position of an instrument relative to an area of interest. The system includes an instrument and an instrument guide mounted to the instrument. The instrument guide carries a first localizer proximate the instrument. The first localizer is movable relative to the instrument. The system also includes a fixator configured to be attached to the area of interest. The fixator carries a second localizer proximate the area of interest. The second localizer is movable relative to the area of interest. The first and second localizers are movable in order that the first and second localizers are in communication such that the position of one of the first and second localizers is known relative to the position of the other of the first and second localizers.

8 Claims, 5 Drawing Sheets

ADJUSTABLE INSTRUMENTS FOR USE WITH AN ELECTROMAGNETIC LOCALIZER

This application is related to, and claims priority from, Provisional Application No. 60/417,960 filed Oct. 11, 2002, titled "Repositionable Instruments and Fixator For Use With Electromagnetic Localization," the complete subject matter of which is incorporated herein by reference in its entirety.

BACKGROUND OF THE INVENTION

The present invention relates to adjustable instruments for use with a localizing device. More particularly, certain embodiments of the present invention relate to an adjustable drill guide and an adjustable fixator for use with an electromagnetic localizing system during surgery.

During surgical operations, it is beneficial to be able to track the direction and progress of a surgical instrument, such as a drill bit, into a patient's body in order to ensure that the instrument is directed into the appropriate point in the body. Therefore, surgical tracking systems have been developed that are able to display and monitor movement of a surgical instrument relative to an image of the patient's body.

One system used for surgical tracking is an electromagnetic tracking system. In a typical electromagnetic tracking system, the area of the patient's body where surgery is to take place is imaged using an imaging technology such as an MRI, X-ray, CT scan or any other appropriate imaging method. The scanned images are stored in a computer system and are displayed on a screen during the surgical procedure. Localizing devices are then used to track the movement of surgical instruments relative to the patient's body. For example, a transmitter that emits an electromagnetic field is secured to the patient's body proximate the area of the patient's body where surgery is to take place. Typically, the transmitter is secured to a fixator that is fixedly attached to the patient's bone by bone screws. The instrument that is to be tracked during surgery has a receiver mounted thereto that receives the electromagnetic signals from the transmitter. The transmitter and receiver are both connected to the computer that displays the image. The computer translates the location of the transmitter on the patient's body to an equivalent point on the image. Then, by monitoring the signals sent from the transmitter to the receiver as the instrument is used in surgery, the computer is able to track the movement of the instrument relative to the transmitter and transpose the movement to the image. Therefore, medical personnel may closely track the positioning and progress of the instrument at the patient's body during surgery by examining the image.

Alternatively, in some electromagnetic systems, a receiver is placed on the patient and the instrument, and a field transmitter is placed proximate the patient. The receivers and transmitter are connected to the computer, and the computer is then able to track the movements of the instrument on an image similarly to the system using just a single receiver.

However, the conventional electromagnetic tracking systems suffer from some drawbacks. The transmitter and receiver are restricted in the distances that they may be situated apart and the positions in which they may be oriented towards each other. For example, the transmitter and receiver may not effectively communicate when they are situated within a few inches of each other. Conversely, the electromagnetic field created by the transmitter may not reach the receiver if the transmitter and receiver are situated more than about 18 inches from each other. Additionally, the presence of any devices that generate their own electromagnetic fields, such as an electric surgical drill, proximate the tracking system may interfere with the electromagnetic communication between the transmitter and the receiver. Likewise, the presence of some metal objects, such as retractors or operating tables, proximate the tracking system may interfere with the electromagnetic communication between the transmitter and the receiver. The interference is especially pronounced when a metal object is located between the transmitter and receiver. The effect of this interference may be a loss of ability to track with the system or a decrease in the accuracy of the tracking. An operator can avoid the difficulties associated with the orientations of the localizers and the distances between the localizers by carefully placing the localizers relative to one another such that any interference is minimized. However, because the fixator is securely fastened into the patient's bone by screws and the receiver is securely mounted to the instrument, and the instrument must typically be in a specific position to perform the intended surgical task, it can be difficult for an operator to adjust the localizers relative to each other in order to achieve effective electromagnetic communication. Therefore, there is a risk during surgery of a surgeon being unable to track the surgical instrument should an interfering object come near the localizers or should the instrument become positioned too far away from, or too close to the fixator.

Therefore, a need exists for an improved method of positioning the localizers on an instrument and a fixator in order that the localizers can communicate during a surgical procedure.

BRIEF SUMMARY OF THE INVENTION

Certain embodiments of the present invention include a system for tracking the position of an instrument relative to an area of interest. The system includes an instrument and an instrument guide mounted to the instrument. The instrument guide carries a first localizer proximate the instrument. The first localizer is movable relative to the instrument. The system also includes a fixator configured to be attached to the area of interest. The fixator carries a second localizer proximate the area of interest. The second localizer is movable relative to the area of interest. The first and second localizers are movable in order that the first and second localizers are in communication such that the position of one of the first and second localizers is known relative to the position of the other of the first and second localizers.

Certain embodiments of the present invention include a tracking system. The tracking system includes a surgical instrument, a computer system that stores an image of an area of interest of a patient's body, and an instrument guide mounted to the surgical instrument. The instrument guide includes a stem configured to carry a first localizer a fixed distance from the surgical instrument. The first localizer is connected to the computer. The stem is movable relative to the rest of the instrument guide. The system includes a fixator connected to a bone in the area of interest. The fixator includes a post configured to carry a second localizer proximate the area of interest. The second localizer is connected to the computer. The post is movable relative to the area of interest. The first and second localizers are movable in order that the first and second localizers are in communication such that the computer system calculates the position of the first localizer relative to the position of the second localizer and the image.

Certain embodiments of the present invention include a method for using an electromagnetic localizing system. The method includes taking an image of an area of interest of a patient's body and storing the image on a computer system. The method further includes providing a surgical instrument and providing an instrument guide that is connected to the surgical instrument. The instrument guide has a localizer assembly that carries a receiver thereon, and the receiver is connected to the computer. The localizer assembly is movable relative to the rest of the instrument guide. The method further includes providing a fixator that is attached to the area of interest of the patient. The fixator has a transmitter post that carries a transmitter thereon. The transmitter is connected to the computer, and the post is movable relative to the area of interest. The method further includes adjusting the positions of the localizing assembly and post in order that the transmitter and the receiver, respectively, are in electromagnetic communication such that the computer system may calculate the position of the receiver relative to the transmitter and the image.

Figure 1:
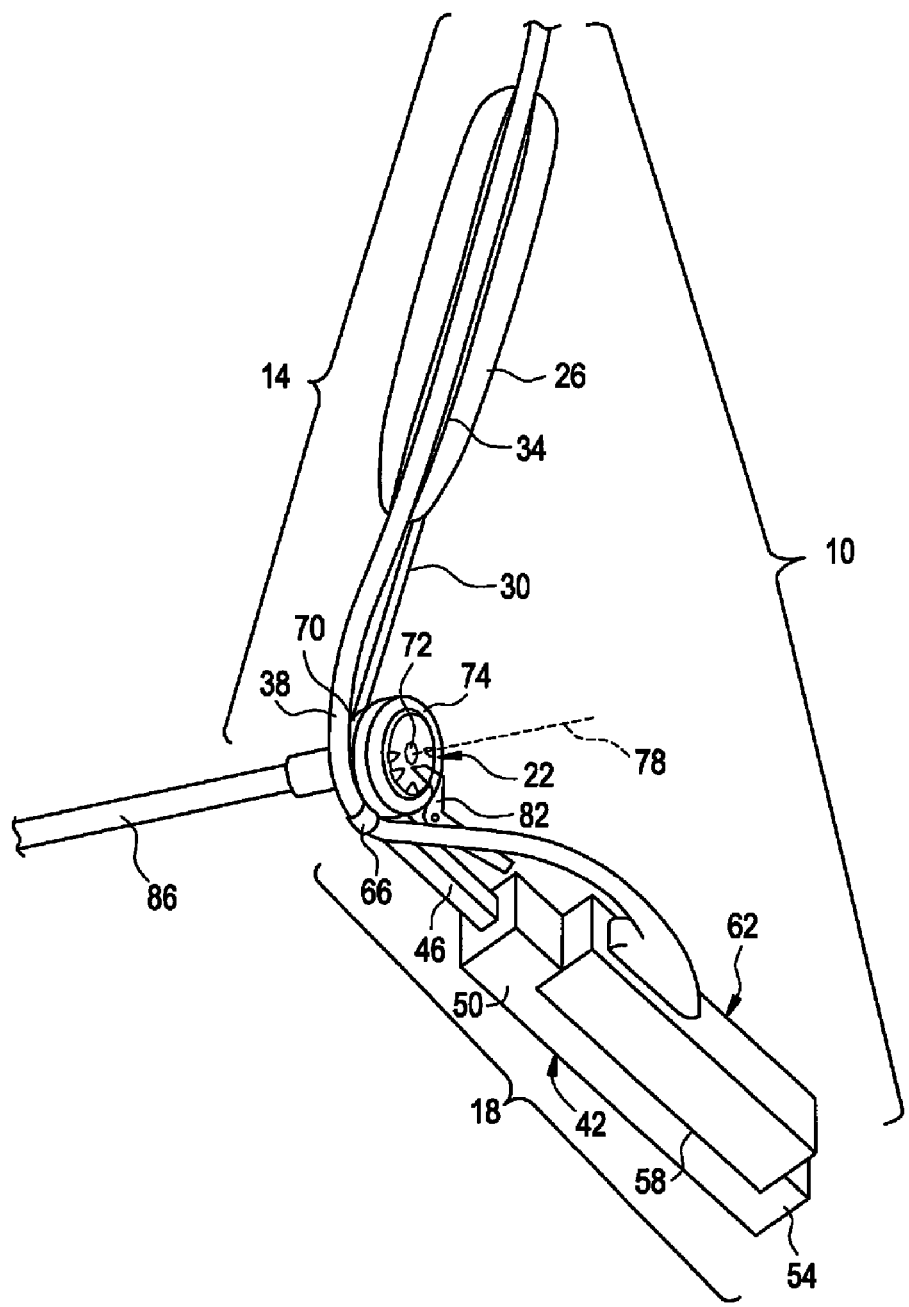
FIG. 1 is an isometric view of a drill guide formed according to an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

FIG. 1 is an isometric view of a drill guide 10 formed according to an embodiment of the present invention. The drill guide 10 includes a handle assembly 14 connected to a localizer assembly 18 at a collar section 22. The handle assembly 14 includes a rounded handle 26 mounted to a handle stem 30. The handle stem 30 extends from the collar section 22. The handle 26 has a groove 34 that receives a cord 38 extending along the stem 30 from the localizer assembly 18. The localizer assembly 18 includes a mounting block 42 mounted to a localizer stem 46. The localizer stem 46 extends from the collar section 22. The mounting block 42 includes a block 50 and a foot 54 separated by a gap 58. The mounting block 42 receives a localizer or an electromagnetic receiver 62 in the gap 58 such that the receiver 62 is secured between the block 50 and the foot 54. The receiver 62 is configured to receive electromagnetic signals. The receiver 62 is electrically connected to a computer system (not shown) by the cord 38. The cord 38 extends from the receiver 62 to the collar section 22 and is secured to the collar section 22 by a clip 66. The cord 38 is secured in the clip 66 and the handle 26 such that the cord 38 does not hang loosely from the drill guide 10.

The collar section 22 includes a circular first collar 70 connected to a circular second collar 74. The first and second collars 70 and 74 are concentrically aligned with each other in order to define a central bore 72 along a longitudinal axis 78. The handle stem 30 is connected to the first collar 70 and the localizer stem 46 is connected to the second collar 74. The first and second collars 70 and 74 rotate relative to each other about the longitudinal axis 78. The collar section 22 includes a locking mechanism 82 that may be manipulated to secure the first and second collars 70 and 74 to each other such that the first and second collars 70 and 74 may not be rotated relative to each other. A removable guide sleeve 86 with a bore (not shown) is rigidly attached to the first collar 70 such that the bore of the guide sleeve 86 aligns with the central bore 72 of the first and second collars 70 and 74 and with the longitudinal axis 78.

Figure 2:
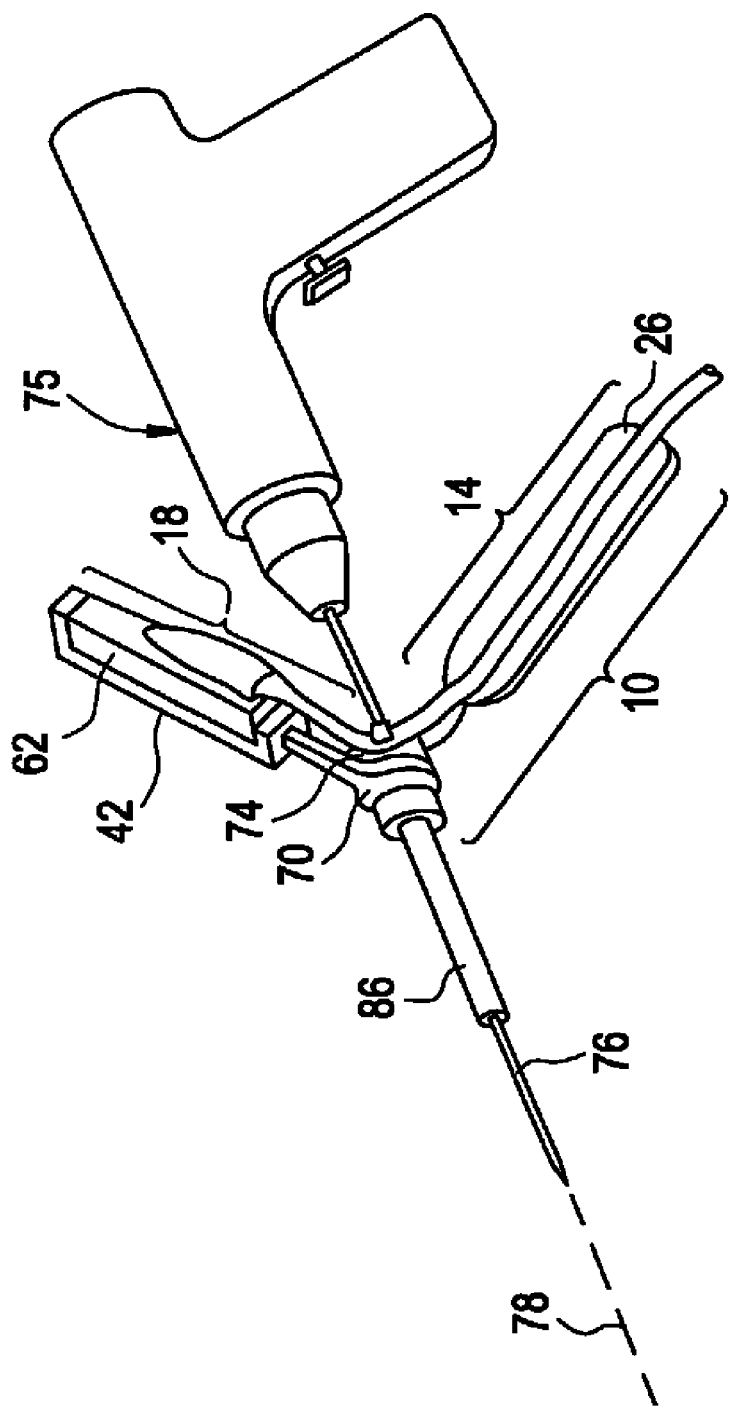
FIG. 2 is an isometric view of a drill guide and a drill formed according to an embodiment of the present invention.

FIG. 2 is an isometric view of the drill guide 10, a drill 75, and drill bit 76 formed according to an embodiment of the present invention. The drill bit 76 is connected to the drill 75 and extends along the longitudinal axis 78, through the central bore 72 (FIG. 1) of the drill guide 10 and through the bore of the guide sleeve 86. The position of the receiver 62 on the mounting block 42 is fixed and known relative to the longitudinal axis 78. Therefore, the computer is able to calculate the position of the bore of the guide sleeve 86 by communicating with the receiver 62 and may thus track the trajectory of the drill bit 76. The surgeon may adjust the position of the receiver 62 on the drill guide 10 by releasing the locking mechanism 82 (FIG. 1). The surgeon may then rotate the localizer assembly 18 around the longitudinal axis 78 until the receiver 62 is in a desirable position. The surgeon may use the handle 26 with one hand to direct the drill guide 10 during surgery. The surgeon may release the locking mechanism 82 in order to rotate the handle assembly 14 about the collar section 22 until the handle 26 is located in a desirable position. When the handle assembly 14 and the localizer assembly 18 are properly positioned, the surgeon may engage the locking mechanism 82 such that the first and second collars 70 and 74 do not move. Thus, the surgeon may lock the handle 26 and the receiver 62 in the desired positions relative to one another.

Figure 3:
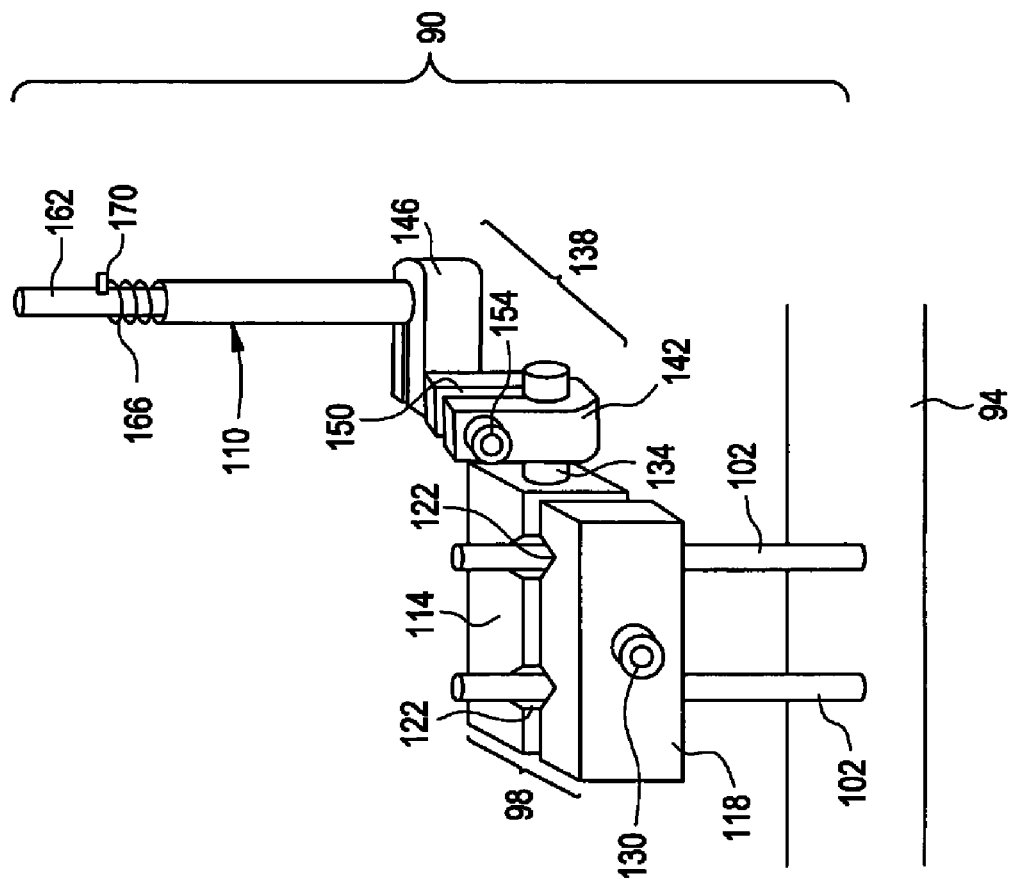
FIG. 3 is an isometric view of a fixator formed according to an embodiment of the present invention.

FIG. 3 is an isometric view of a fixator 90 extending from the soft tissue 94 of a patient formed according to an embodiment of the present invention. The fixator 90 includes an attachment block 98, bone screws 102, a locking universal joint 138, and a transmitter post 110. The screws 102 are positioned through the soft tissue 94 into the patient's bone (not shown). The surgeon considers three factors when determining where to insert the bone screws 102: 1) the rigidity of the insertion in the bone, 2) the effect of the insertion on the patient's tissues, and 3) the optimum location for tracking the receiver 62 (FIG. 1) with a minimum of electromagnetic interference. The first and second criteria are known to surgeons. The third criterion requires experience with electromagnetic tracking technology and its use in proximity to the standard operating room environment. For example, the surgeon must consider the proximity, design, and composition of the operating room table, retractors, instruments, and any other potential sources of electromagnetic interference during the procedure.

Once the surgeon has determined a proper site for the bone screws 102, the surgeon inserts the bone screws 102 percutaneously and under sterile conditions into the bone. Preferably, the bone screws 102 are Schanz pins, which are frequently used in orthopedic surgery and have smooth shafts and threaded ends, however, any number of other fasteners may be used. A drill guide 10 may be used to direct the placement of the drill holes into the bone with proper spacing. A T-handle driver (not shown) with a universal chuck is preferably used to insert the bone screws 102 into the bone, however, any number of other drivers or methods may be used.

The bone screws 102 should be long enough to be attached to the bone and still protrude far enough above the surface of the skin 94 to be attached to the fixator 90.

The attachment block 98 includes a main block 114 and a capture plate 118. The main block 114 has parallel V-shaped grooves 122 machined into a peripheral side thereof. Likewise, the capture plate 118 has grooves 122 machined into a corresponding peripheral side thereof. The main block 114 and the capture plate 118 both receive a screw 130 that may be tightened to bring the main block 114 and capture plate 118 toward each other. When the main block 114 and the capture plate 118 are joined together by the screw 130, the two sets of grooves 122 are aligned opposite each other to define channels. The attachment block 98 is positioned about the bone screws 102 such that the grooves 122 receive the bone screws 102. The capture plate 118 is then tightened to the main block 114 by the screw 130 such that the attachment block 98 is rigidly secured to the screws 102 above the tissue 94. In an alternative embodiment, the fixator 90 may be attached to the bone in a number of other ways besides bone screws 102, such as by a clamp or a nail.

A short cylindrical post 134 extends from the main block 114 and is connected to the locking universal joint 138. The locking universal joint 138 includes first and second U-shaped clamps 142 and 146. The first clamp 142 receives the post 134 within a gap 150. The first clamp 142 is connected to the second clamp 146 by a screw 154. The second clamp 146 receives a cylindrical transmitter post 110. Alternatively, a locking ball joint or other mechanism may be used to connect the transmitter post 110 to the main block 114. The transmitter post 110 includes a shaft 162 having a spring 166 and dowel pin 170 mechanism at an end opposite the second clamp 146. A transmitter (not shown) is mounted to the shaft 162 such that the dowel pin 170 engages the transmitter and the spring 166 is loaded between the transmitter and the transmitter post 110 to hold the transmitter rigidly to the transmitter post 110. Alternatively, the transmitter post 110 may be a series of rigid shafts or links with locking joints, or any number of other attachment mechanisms, that allow the transmitter to be placed rigidly in a position relative to the main block 114.

Figure 4:
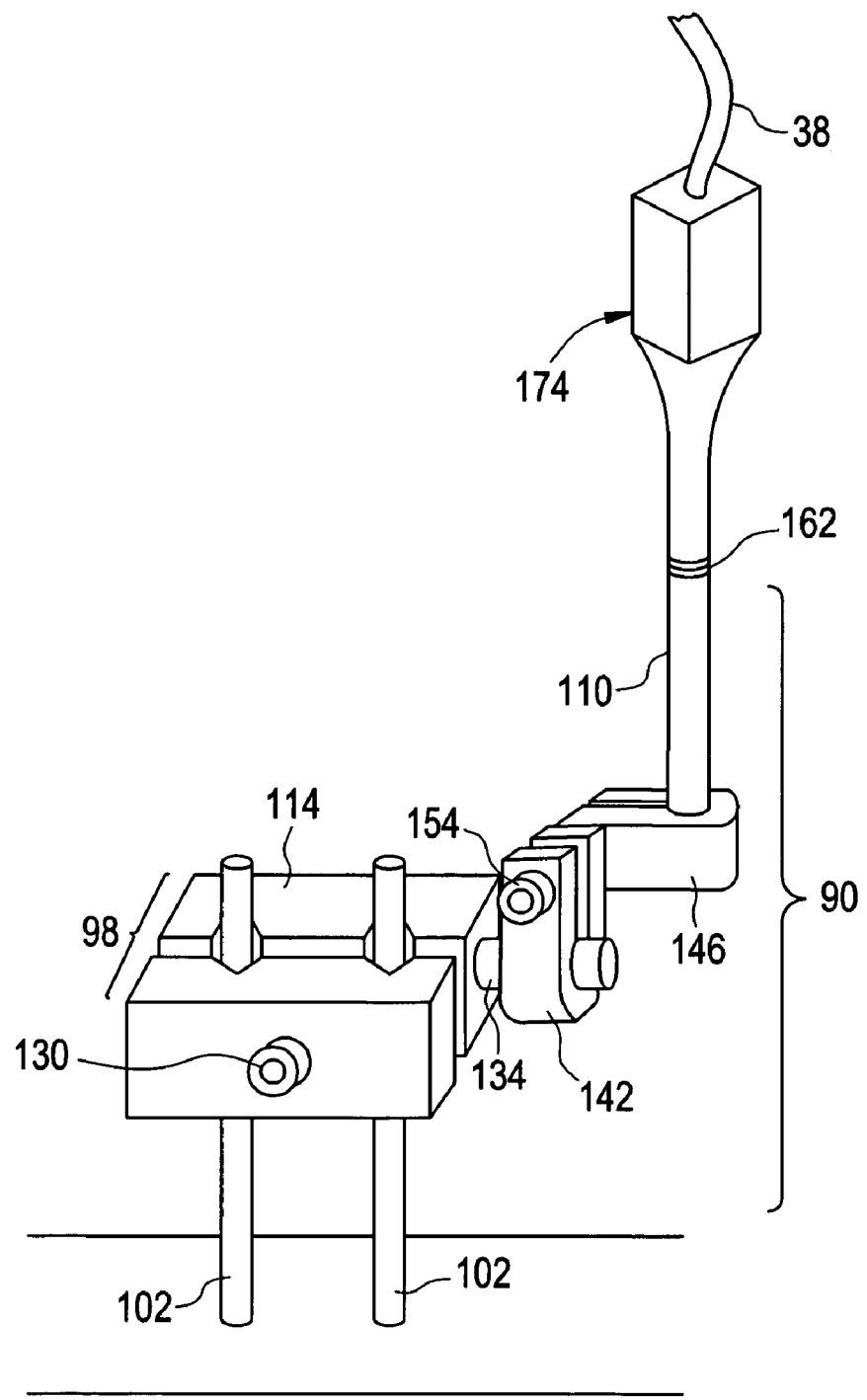
FIG. 4 is an isometric view of a fixator and a transmitter formed according to an embodiment of the present invention.

FIG. 4 is an isometric view of the fixator 90 and a localizer or an electromagnetic transmitter 174 formed according to an embodiment of the present invention. The transmitter 174 is connected to the transmitter post 110 along the shaft 162 and is thus rigidly attached to the bone. A cord 38 extends from the transmitter 174 to the computer (not shown). The transmitter 174 is configured to emit electromagnetic signals. The first and second clamps 142 and 146 may be adjusted such that the transmitter 174 is positioned at different orientations to the attachment block 98. For example, the first clamp 142 may be rotated about the post 134 and the second clamp 146 may be rotated about the screw 154 to adjust the position of the transmitter 174. Also, the transmitter post 110 may be slid within the gap 150 of the second clamp 146 to adjust the effective length of the transmitter post 110 extending from the universal locking joint 138. Alternatively, the length of the transmitter post 110 may be adjusted or a number of transmitter posts 110 having different lengths may be substituted for each other in the second clamp 146. Alternatively, an operator may loosen the screw 130 in the attachment block 98 to change the position of the attachment block 98 on the bone screws 102. In an alternative embodiment, the transmitter post 110 may have two or more links with locking universal joints connecting each link. Alternatively, additional assemblies having a universal joint 138 and rod of the same diameter as post 134 may be inserted between the main block and the transmitter post 110 to provide extended reach and adjustability. Additionally, other methods of adjustably and rigidly holding the transmitter 174 relative to the bone may be employed.

Figure 5:
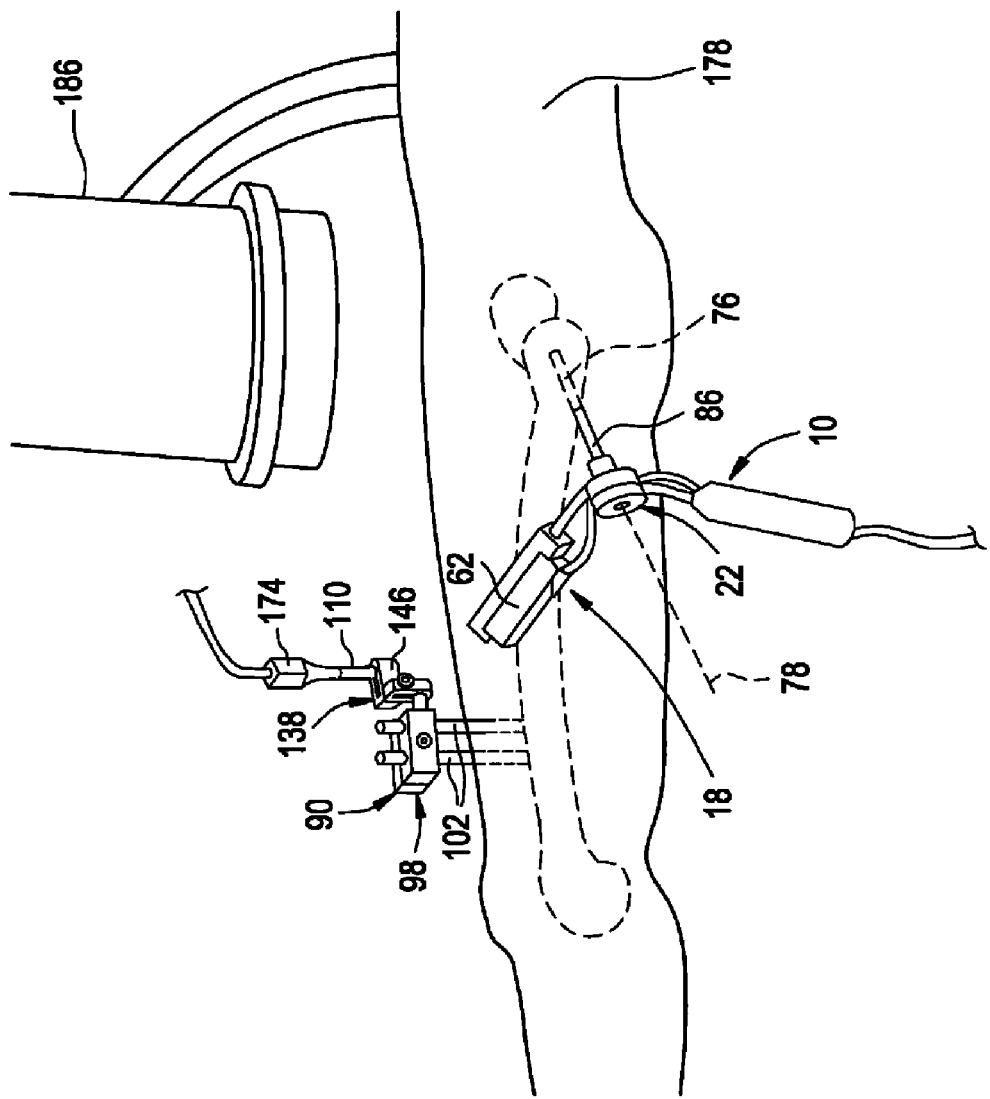
FIG. 5 is an isometric view of a drill guide and a fixator as used in a surgical procedure formed according to an embodiment of the present invention.

FIG. 5 is an isometric view of the drill guide 10 and fixator 90 as used in a surgical procedure. A patient 178 lies on an operating table. The fixator 90 is affixed to the patient's femur proximal the medial epicondyle and carries the transmitter 174. A movable C-arm x-ray imaging device 186 is positioned above the patient 178. The C-arm 186 is connected to the computer system (not shown). Alternatively, other types of imaging devices may be configured to take any number of different kinds of images including x-rays, MRIs, and CT scans. The C-arm 186 takes x-ray images of the patient 178 and the images are stored on the computer system. The C-arm 186 is configured with a localizer (not shown) to determine the location of the images relative to the transmitter 174. The fixator 90 may be adjusted to optimize the relative positioning of the localizer in the C-arm 186 and the transmitter 174 affixed to the patient.

The surgeon may then bring the drill (not shown) proximate the patient to begin operating. The transmitter 174 sends signals to the receiver 62 mounted on the drill guide 10. The surgeon may check the computer system to see whether the transmitter 174 and receiver 62 are in communication. If the receiver 62 is receiving the signals from the transmitter 174, the surgeon may begin using the drill to operate on the patient. If the receiver 62 is not effectively receiving signals from the transmitter 174, the surgeon may adjust the position of the receiver 62 on the drill guide 10 or the position of the transmitter 174 on the fixator 90 as described above.

During the operation, the transmitter 174 sends electromagnetic signals to the receiver 62 mounted to the drill guide 10. The computer analyzes the signals received by the receiver 62 to calculate the position of the receiver 62 relative to the transmitter 174. Because the receiver 62 is a fixed and known distance from the longitudinal axis 78 of the drill guide 10, the computer may also calculate the position of the drill guide 10 relative to the transmitter 174. By tracking the position of the drill guide 10 relative to the transmitter 174, the computer is able to recreate the position of the guide sleeve 86 and the trajectory of the drill bit 76 on the images. Thus, the surgeon can observe the position and movement of the drill guide 10 on the images in order to avoid directing the drill bit 76 into wrong areas of the patient's body.

During surgery the computer system may indicate that the transmitter 174 and the receiver 62 are no longer in communication. The transmitter 174 and receiver 62 may be positioned too far away from each other or some interfering object may be positioned proximate either one of them. The surgeon may therefore adjust the position of either the receiver 62 or the transmitter 174 until they are effectively back in communication. For example, the surgeon may unlock the collar section 22 such that the localizer assembly 18 may be rotated about the longitudinal axis 78 until the receiver 62 is better positioned to receive signals from the transmitter 174. Also, the surgeon may be able to adjust the position of the transmitter post 110 within the second clamp 146, the position of the locking universal joint 138 or the attachment block 98 relative to the bone screws 102 to better position the transmitter 174 to communicate with the receiver 62. By adjusting the positions of the receiver 62 and the transmitter 174 in such ways, the surgeon can optimize communication between the transmitter 174 and the receiver 62. Furthermore, by adjusting the positions of the receiver 62 and the transmitter 174 in such way, the surgeon can optimize communication between the transmitter 174, receiver 62, and any other localizers used as a part of the tracking system.

In an alternative embodiment, the adjustable fixator and instrument guide may be used with any number of different surgical tools besides a surgical drill. Also, the adjustable fixator and instrument guide may be used to track any number of different instruments, tools, utensils, etc. in any number of procedures, whether medically related or not. Alternatively, the adjustable fixator and instrument guide may be used with different kinds of tracking systems using different kinds of localizers besides electromagnetic localizers. For example, optical tracking systems may be used where the fixator and instrument guide may carry light emitting diodes that are in communication with a digitizer. Alternatively, the fixator and instrument guide may be used with multiple receivers and/or multiple transmitters that may be positioned on the patient, the operating table, or other sites. Alternatively, the transmitter may be positioned on the instrument guide and the receiver may be positioned on the fixator and the movement of the drill guide is tracked by calculating the movement of the transmitter relative to the receiver.

The tracking system of the various embodiments provides several advantages over conventional tracking systems. The adjustability of the fixator 90 and the drill guide 10 provide a surgeon with the ability to address interference issues that occur before or during surgery. By being able to adjust the positions of the localizers during surgery, the surgeon is able to overcome interference and distance problems and maintain the tracking of the surgical device on the images. For example, the position of the first localizer on the instrument may be adjusted relative to the instrument and the position of the second localizer on the fixator may be adjusted relative to the fixator such that the positions of the first and second localizers relative to each other is adjusted to optimize communications therebetween. Furthermore, the position of the first localizer on the instrument may be adjusted relative to the instrument and the position of the second localizer on the fixator may be adjusted relative to the fixator such that the positions of the first and second localizers relative to a third localizer may be adjusted to optimize communications between all three localizers. Therefore, the surgeon is able to reduce the risk of electromagnetic interference or localizer separation affecting the surgeon's ability to direct and operate the surgical drill in a safe and proper manner.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for tracking the position of an instrument relative to an area of interest, comprising:
an instrument;
an instrument guide mounted to said instrument, said instrument guide having an elongated handle extending at an angle relative to a longitudinal axis of a guide sleeve and carrying a first localizer proximate said instrument, said first localizer being movable relative to said instrument and rotatable with respect to said elongated handle, said elongated handle being rotatable with respect to said first localizer;
a fixator configured to be attached to the area of interest, said fixator carrying a second localizer proximate said area of interest, said second localizer being movable with respect to the fixator, said first and second localizers being movable in order that one of said first and second localizers directly communicates with the other of said first and second localizers such that the position of one of said first and second localizers is known relative to the position of the other of said first and second localizers;
wherein the instrument guide includes a localizer assembly that is connected to said elongated handle at concentric collars, said collars receiving said instrument along a longitudinal axis, said localizer assembly carrying said first localizer, said collars being rotatable relative to each other such that said first localizer is rotatable about said longitudinal axis relative to said instrument and elongated handle;
wherein said fixator includes a block receiving screws in channels therein, said second localizer being connected to said block and said screws being inserted into the area of interest, said block being adjustable along said screws in order to adjust the position of said second localizer relative to the area of interest;
wherein said fixator includes first and second clamps and a post, said first and second clamps being adjustably connected to said block and each other and said post being adjustably connected to said first and second clamps, said post receiving said second localizer such that said second localizer is adjustable relative to said block along said first and second clamps and said post;
wherein the concentric collars define a central bore;
wherein the concentric collars comprise a first collar and a second collar;
wherein the guide sleeve and the elongated handle are rigidly attached to the first collar;
wherein a bore of the guide sleeve defines the central bore; and
wherein the first localizer is rigidly attached to the second collar.

2. The system of claim 1, wherein said first localizer is an electromagnetic receiver and said second localizer is an electromagnetic transmitter, said transmitter and receiver being connected to a computer that analyzes the communications therebetween to calculate the position of said receiver relative to said transmitter.

3. The system of claim 1, further including an imaging device that takes images of the area of interest, said images being stored on a computer system that calculates the position of said second localizer on said images and calculates the position of said first localizer relative to said images.

4. The system of claim 1, wherein said instrument is a surgical drill guide and the area of interest is an area of a patient's body, said first and second localizers being connected to a computer carrying images of the area of interest, said computer analyzing the communication between said first and second localizers to calculate the position of said instrument relative to said images.

5. The system of claim 1, wherein said first and second localizers are light emitting diodes.

6. The system of claim 1, wherein said fixator includes a post, said post having a shaft with a spring and dowel mechanism thereon, said second localizer receiving said shaft such that said dowel engages said second localizer and said spring is loaded between said second localizer and said post to secure said second localizer to said post.

7. The system of claim 1, wherein the position of the first localizer relative to the instrument and the position of the second localizer relative to the fixator may be adjusted such that the positions of the first and second localizers relative to each other may be adjusted to optimize communication therebetween.

8. The system of claim 1, wherein the position of the first localizer relative to the instrument and the position of the second localizer relative to the fixator may be adjusted such that the positions of the first and second localizers relative to a third localizer may be adjusted to optimize communication between the three localizers.

* * * * *